United States Patent [19]

Dines et al.

[11] 4,429,111
[45] * Jan. 31, 1984

[54] LAYERED ORGANOPHOSPHORUS INORGANIC POLYMERS CONTAINING MIXED FUNCTIONAL GROUPS

[75] Inventors: Martin B. Dines, Santa Ana; Peter M. DiGiacomo, Mission Viejo, both of Calif.

[73] Assignee: Occidental Research Corporation, Irvine, Calif.

[ * ] Notice: The portion of the term of this patent subsequent to Nov. 4, 1997 has been disclaimed.

[21] Appl. No.: 268,408

[22] Filed: May 29, 1981

Related U.S. Application Data

[63] Continuation of Ser. No. 60,250, Jul. 24, 1979, which is a continuation-in-part of Ser. No. 945,971, Sep. 26, 1978, Pat. No. 4,232,146.

[51] Int. Cl.³ .................... C08G 79/04; C08G 79/00
[52] U.S. Cl. ........................... 528/395; 260/429.3; 260/429 R; 260/429 J; 260/435 R; 260/429.7; 260/429.5; 528/398
[58] Field of Search ................. 528/395, 398; 260/429.3, 429.5, 435 R, 429 R, 429 J, 429.7

[56] References Cited

U.S. PATENT DOCUMENTS

| | | | |
|---|---|---|---|
| 2,512,063 | 6/1950 | Kreidl et al. | 528/395 |
| 3,231,347 | 1/1966 | Revukas | 44/69 |
| 3,415,781 | 12/1968 | Block et al. | 528/395 |
| 3,445,492 | 5/1969 | Washburn et al. | 260/429 |
| 3,491,133 | 1/1970 | Revukas | 260/429 |
| 3,615,807 | 10/1971 | Yates | 106/288 B |
| 3,634,479 | 1/1972 | Ridenour | 260/429.7 |
| 3,663,460 | 5/1972 | Block et al. | 260/33.6 R |
| 3,681,265 | 8/1972 | Krueger | 528/271 |

FOREIGN PATENT DOCUMENTS

| | | |
|---|---|---|
| 2614356 | 10/1977 | Fed. Rep. of Germany . |
| 539293 | 9/1941 | United Kingdom . |
| 1406419 | 9/1975 | United Kingdom . |
| 170968 | 6/1965 | U.S.S.R. . |

OTHER PUBLICATIONS

Chem. Abstract 83, 70750g, (1975).
Chem. Abstract 85, 13433y, (1976).
Chem. Abstract 86, 155758c, (1977).
Chem. Abstract 58, 1487b, (1963).
Chem. Abstract 55, 11161c, (1961).
Dub, "Organometallic Compounds," Springer-Verlog, Berlin VIII, pp. 187-191, (1962).
Doak, et al., "Organometallic Compounds of Arsenic, Antimony and Bismuth," Wiley, Intersc., N.Y. pp. 46-49, (1970).
Journal of Inorganic & Nuclear Chemistry, vol. 40, pp. 1113-1117, Jun. 1978, (Costantino et al.).

*Primary Examiner*—Wilbert J. Briggs, Sr.
*Attorney, Agent, or Firm*—Christie, Parker & Hale

[57] ABSTRACT

Layered solid inorganic polymers having at least one organo group anchored to a surface of the polymer, and which can be useful in catalysis, lubrication, ion-exchange, chromatography and absorption processes, can be made by reacting at least one tetravalent metal (e.g., zirconium, cerium, thorium, uranium, lead, hafnium, titanium, etc.) and two or more acids selected from phosphoric acid, phosphonic acid and organophosphorus acids of the formula $((HO)_2OP)_nR$ wherein n is 1 or 2 and R is an organo group covalently bonded to the phosphorus atom. Preferably the reaction is conducted with a stoichiometric excess of phosphorus acids in a liquid medium in which a compound of the metal is soluble. The covalent bonding can be through oxygen to produce phosphates, or through carbon to produce phosphonates.

33 Claims, 8 Drawing Figures

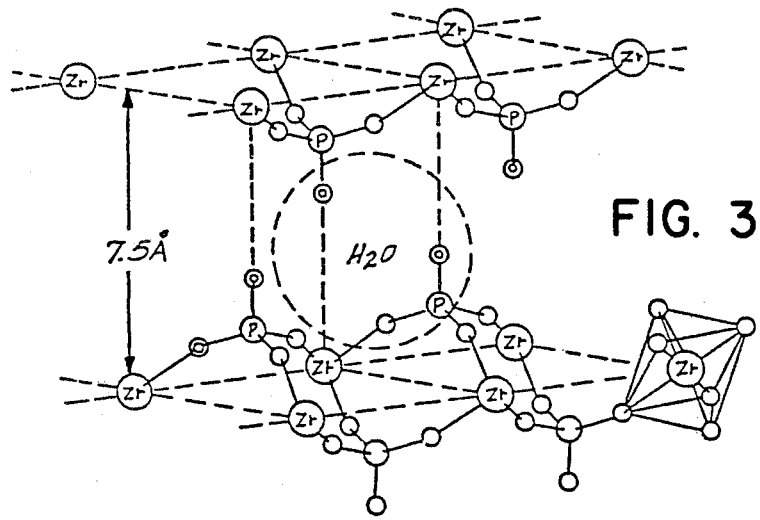
FIG. 3
FIG. 5
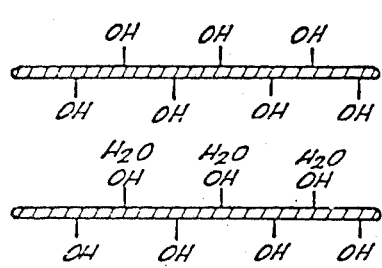
FIG. 4
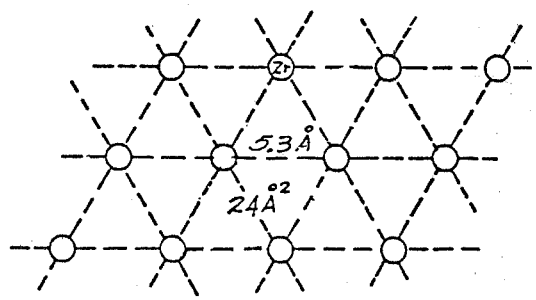
FIG. 6
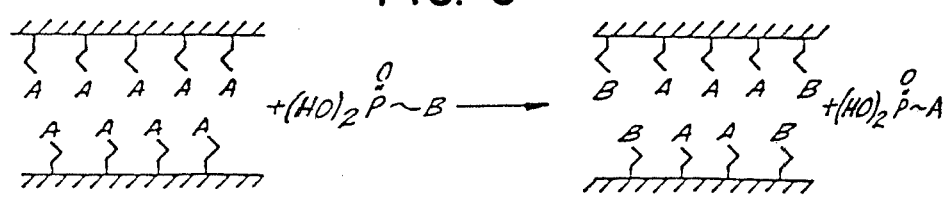

LAYERED ORGANOPHOSPHORUS INORGANIC POLYMERS CONTAINING MIXED FUNCTIONAL GROUPS

CROSS-REFERENCE TO RELATED APPLICATIONS

This application is a continuation of application Ser. No. 60,250, filed July 24, 1979, which is a continuation-in-part of application Ser. No. 945,971, filed Sept. 26, 1978, now U.S. Pat. No. 4,232,146, issued Nov. 4, 1980, and is related to the following copending applications: Ser. No. 952,228 filed Oct. 17, 1978 now U.S. Pat. No. 4,235,990 issued Nov. 25, 1980; Ser. No. 966,197 filed Dec. 4, 1978 now U.S. Pat. No. 4,235,991 issued Nov. 25, 1980; Ser. No. 7,275 filed Jan. 29, 1979, Ser. No. 43,910 filed May 30, 1979 and titled Process for Preparing Layered Organophosphorus Inorganic Polymers; Ser. Nos. 54,107 and 54,097 filed July 2, 1979 and titled, respectively, Layered Cyano End Terminated Organophosphorus Inorganic Polymers and Layered Organophosphorus Inorganic Polymers Containing Mercapto or Thio Groups; and four applications filed concurrently herewith on July 24, 1979, and titled Layered Organophosphorus Inorganic Polymers Containing Cyclic Groups Ser. No. 60,077; Layered Organoarsenous Inorganic Polymers Ser. No. 60,078; Layered Organophosphorus Inorganic Polymers Containing Acyclic Groups Ser. No. 60,079; and Layered Organophosphorus Inorganic Polymers Containing Oxygen Bonded to Carbon Ser. No. 60,249. The entire disclosure of each of these applications is hereby incorporated herein by this reference.

BACKGROUND OF THE INVENTION

The present invention is directed to solid inorganic polymers having organo groups anchored to the surfaces of the polymers. The majority of the polymers formed are layered crystals which display intercalation activity.

The interface surfaces of solids are responsive regions of chemical and physical action. In many practical chemical and physical phenomena such as absorption, corrosion, inhibition, heterogeneous catalysis, lubrication, ion exchange activity, adhesion and wetting and electrochemistry activity occurs as a consequence of the presence of a definable solid surface. Solid agents are preferred in most processes over solution or homogeneously dispersed reactive alternatives primarily because they greatly simplify efficient separation of products from reactants. However, solids invariably suffer from deficiencies in activity and selectivity in the conversions they effect, due to inherent heterogeneity in their active sites which arises from the nature of their surface structure. Furthermore, much of the active sites are usually buried within the surface, and as a result of these two factors, elevated temperature and low conversions are typically encountered. Exceptions in which homogeneous catalysts are employed have been the Monsanto process for the production of acetic acid from methanol and carbon monoxide employing rhodium, the production of linear alcohols from olefins and syngas, ethylene oxidation by the Wacker process, catalysis of olefins to form polymers, and other polymerization systems.

In an effort to achieve the best features of both homogeneous and heterogeneous processes, efforts have been made to chemically "anchor" known effective solution agents such as phosphines, nitriles, cyclopentadiene and the like, onto certain solids. Porous inorganic surfaces and insoluble organic polymers have been employed. Silica has been the inorganic of choice, the bonded ligand being attached by reaction with the —OH groups projecting from the surface. The organic polymer most used has been polystyrene, with an appropriate metal-coordinating function bonded via the phenyl rings. Results have been generally encouraging. However, there have been pervasive problems deriving from the non-uniform situation of sites which has manifested itself in loss of expected selectivity, activity and even in attrition.

Efforts at heterogenizing catalysts have been discussed by Bailar, "Heterogenizing Homogeneous Catalysts," Catalysis Reviews—Sci. & Eng. 10(1) 17-35 (1974) and Hartley and Vezey, "Supported Transition Metal Complexes as Catalysts," Advances in Organometallic Chemistry 15, 189-235(1977). The entire disclosure of which is incorporated herein.

Many inorganic solids crystallize with a layered structure and some could present sites for anchoring active groups. In this form, sheets or slabs with a thickness of from one to more than seven atomic diameters lie upon one another. With reference to FIG. 1, strong ionic or covalent bonds characterize the intrasheet structure, while relatively weak van der Waals or hydrogen bonding occurs between the interlamellar basal surfaces, in the direction perpendicular to their planes. Some of the better known examples are prototypal graphite, most clay minerals, and many metal halides and sulfides. A useful characteristic of such materials is the tendency to incorporate "guest" species in between the lamella.

In this process, designated "interclalation", the incoming guest molecules, as illustrated in FIG. 2, cleave the layers apart and occupy the region between them. The layers are left virtually intact, since the crystals simply swell in one dimension, i.e., perpendicular to the layers. If the tendency to intercalate is great, then the host layered crystal can be thought of as possessing an internal "super surface" in addition to its apparent surface. In fact, this potential surface will be greater than the actual surface by a factor of the number of lamella composing the crystal. This value is typically on the order of $10^2$–$10^4$. Although edge surface is practically insignificant compared to basal surface, it is critical in the rate of intercalation, since the inclusion process always occurs via the edges. This is because bonding within the sheets is strong, and therefore, basal penetration of the sheets in an unlikely route into the crystal.

Previous studies of the intercalative behavior of layered compounds have mainly been conducted by solid-state chemists interested in the bulk effects on the layered host materials. Graphite has, for example, been extensively studied from an electronic point of view. In general, the function of the host is essentially passive. That is, on intercalation the host serves as the matrix or surface with which the incoming guest molecules interact, but throughout the process on deintercalation the guests undergo only minor perturbation.

In order for a more active process to occur during intercalation, such as selective complexation or catalytic conversion, specific groups must be present which effect such activity. There might also be some preferable geometric environment about each site, as well as some optimal site-site spacing. These considerations have not been extensively applied to intercalation chemistry simply because such kinds of active groups required are not found on layered surfaces.

An approach in which catalytically active agents have been intercalated into graphite or clays for subsequent conversions has been described in "Advanced Materials in Catalysis", Boersma, Academic Press, N.Y. (1977), Burton et al, editors, and "Catalysis in Organic Chemistry", Pinnavia, Academic Press, N.Y. (1977), G. V. Smith, editor, each incorporated herein by reference. In neither case could it be shown that any activity was occurring within the bulk of the solid. Rather, it is believed that edge sites are responsible for the reactivity observed. In none of the cases was the active site covalently anchored, or fixed upon the lamella of the host. Instead, the normal ion or van der Waals forces of intercalated guests were operating.

One of the few layered compounds which have potential available sites is zirconium phosphate $Zr(O_3POH)_2$. It exists in both amorphous and crystalline forms which are known to be layered. In the layered structure, the site-site placement on the internal surfaces is about 5.3 Å, which leads to an estimated 25 Å$^2$ area per site. This area can accommodate most of the functional groups desired to be attached to each site. The accepted structure, symbolized projection of a portion of a layer of this inorganic polymer and a representation of an edge view of two layers, are shown respectively in FIGS. 3, 4 and 5.

Besides the advantageous structural features of zirconium phosphate, the material is chemically and thermally stable, and non-toxic.

Quite a bit of work has been conducted on the zirconium phosphate, mainly because it has been found to be promising inorganic cation exchanger for alkali, ammonium and actinide ions, Alberti, "Accounts of Chem. Research", 11, 163 (1978), incorporated herein by reference. In addition, some limited work has been described on the reversible intercalation behavior of layered zirconium phosphate toward alcohols, acetone, dimethylformamide and amines, Yamaka and Koizuma, "Clay and Clay Minerals" 23, 477 (1975) and Michel and Weiss, "Z. Natur," 20, 1307 (1965) both incorporated herein by reference. S. Yamaka described the reaction of this solid with ethylene oxide, which does not simply incorporate between the layers as do the other organics, but rather was found to irreversibly react with the acidic hydroxyls to form a covalently bonded product, Yamaka, "Inorg. Chem." 15, 2811, (1976). This product is composed of a bilayer of anchored ethanolic groups aimed into interlayers. The initial layer-layer repeat distance is expanded from about 7.5 Å to 15 Å, consistent with the double layer of organics present. The overall consequence of this reaction is to convert inorganic acid hydroxyls to bound inorganic alkanol groups. This conversion, while of interest, has limited if any improvement over the hydroxyls already available on zirconium phosphate.

A very recently reported effort in the field is Alberti, et al., "J. Inorg. Nucl. Chem.", 40, 1113 (1978) which is incorporated herein by reference. A method similar to that of this invention for the preparation of zirconium bis(benzenephosphonate), zirconium bis(hydroxymethanephosphonate) monohydrate, and zirconium bis(monoethylphosphate) is described, with descriptions of the properties for these products.

Following the Alberti publication, a paper by Maya appeared in "Inorg. Nucl. Chem. Letters", 15, 207 (1979), describing the preparation, properties and utility as solid phases in reversed phase liquid chromatography for the compounds $Zr(O_3POC_4H_9)_2 \cdot H_2O$, $Zr(O_3POC_{12}H_{25})_2$ and $Zr(O_3POC_{14}H_{21})_2$. All of the compositions that are described herein can be useful in gas phase, liquid phase, gas liquid, reversed phase, and bulk and thin layer chromatography. The compounds can also be useful as hosts and carriers for organic molecules and especially biologically active organic molecules (e.g. methoprene).

SUMMARY OF THE INVENTION

This invention relates to mixed component derivatized layered compounds and the uses thereof especially in catalysis. The compounds of the invention have the general formula:

$$M(O_3P\text{-}R)_x(O_3P\text{-}R')_y(O_3P\text{-}R'')_z$$

where $X+Y+Z=2$, M is a tetravalent metal and one of R, R', R'' is an organo group which can be substituted and in which some or all of the hydrogen can be replaced by a halogen (F, Cl, Br, I), the other two can be —OH or —H or an organo group which can be the same or different from R. When R' and/or R'' are OH or H, the compound is preferably prepared as described hereinafter from phosphoric or phosphorous acid.

According to the present invention there is provided solid inorganic polymers having organo groups covalently bonded to phosphorus atoms and in which the phosphorus atoms are, in turn, covalently bonded by oxygen linkage to tetravalent meal atoms and, when formed in a layered crystalline state, provide the organo goups on all of the apparent and interlamellar surfaces.

The process of preparation comprises a liquid medium reaction in which at least one organophosphorus acid compound of the formula:

$$((HO)_2OP)_nR$$

wherein n is 1 or 2 and R is an organo group covalently coupled to the phosphorus atom, and wherein when n is 2, R contains at least two carbon atoms and is directly or indirectly coupled to phosphorus atoms through different carbon atoms whereby the two phosphorus atoms are separated by at least two carbon atoms, is reacted with at least one tetravalent metal ion preferably selected from the group consisting of zirconium, cerium, thorium, uranium, lead, hafnium and titanium. The molar ratio of phosphorous to the tetravalent metal is 2 to 1. Reaction preferably occurs in the presence of an excess of the organophosphorus acid compound and the metal ion is provided as a compound soluble in the liquid medium.

Where only one specie of an organophosphorus acid compound is provided as the reactant with the tetravalent metal compound, the end product will have the empirical formula $M(O_3PR)_2$. Phosphoric and/or phosphorous acid can also be present as reactive dilutants to form part of the solid inorganic polymeric structure which is the product of the reaction.

The products formed are layered crystalline to amorphous in nature. For all products, the R groups may be directly useful or serve as intermediates for the addition or substitution of other functional groups. When the product is crystalline and n is 2, cross-linking between the interlamellar layers occurs.

The normal liquid medium is water. However, organic solvents, particularly ethanol, may be employed where water will interfere with the desired reaction. Preferably, the solvent is the solvent in which the organophosphorus acid compound is prepared. Where the organophosphorus acid compound has a sufficiently low melting point, it can serve as the liquid media.

The metathesis reaction occurs at temperatures up to the boiling point of the liquid medium at the pressures involved, typically from ambient to about 150° C. more preferably from ambient to about 100° C. While formation of the solid inorganic polymer is almost instantaneous, the degree of crystallinity of the product can be increased by refluxing the reaction products for times from about 5 to 15 hours. Crystallinity is also improved by employing a sequestering agent for the tetravalent metal ion.

THE DRAWINGS

Figure 1:
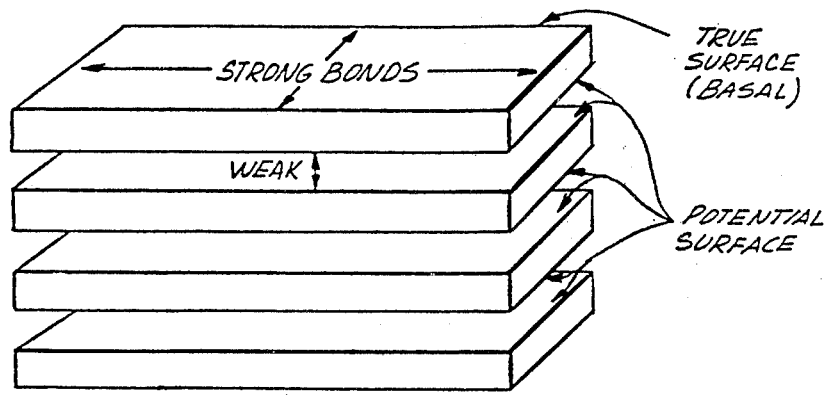
FIG. 1 illustrates a layered microcrystal. Each lamellar slab is formed of strong covalent bonds and has a thickness of about 10 atoms.
Figure 2:
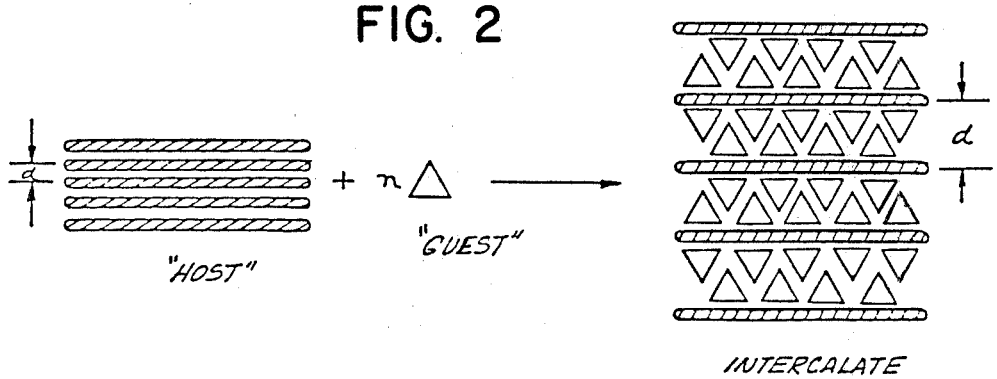
FIG. 2 illustrates intercalation where the interlayer distance is shown as "d."

FIG. 3 illustrates the accepted structure for zirconium phosphate and spacing between layers. The dashed lines between zirconium (Zr) atoms is to establish the plane between them. In the drawing P=phosphorus, O=oxygen and water of hydration is shown.

FIG. 4 illustrates a projection of zirconium plane showing accepted spacing between Zr atoms and the available linkage area.

FIG. 5 is a symbolized depiction of spaced zirconium phosphate layers showing covalently bonded hydroxyl groups and water of hydration.

FIG. 6 illustrates an exchange reaction between anchored groups "A" and groups to be substituted for "B", and ∿ represents the portion of the organo group linking the terminal group "A" or "B" to the crystals or the organophosphorus acid compound reactant.

Figure 7:
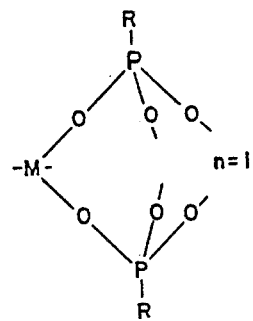

FIG. 7 shows the basic structural unit of the inorganic polymer formed by the process of the invention where n is 1 and where P=phosphorus atom, O=oxygen atom, M=tetravalent metal atom and R is the organo group.

Figure 8:
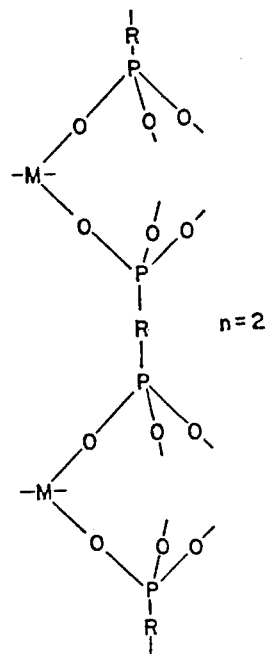

FIG. 8 shows the basic structural unit of the inorganic polymer formed by the Process of the invention where n is 2 and where P=phosphorus atom, O=oxygen atom, M—tetravalent metal atom and R is the organo group.

DETAILED DESCRIPTION

According to the present invention there is provided solid inorganic polymers in layered crystalline to amorphous state by the liquid phase metathesis reaction of at least one organophosphorus acid compound having the formula:

$$[(HO)_2OP]_nR$$

wherein n is 1 or 2 and R is an organo group covalently coupled to the phosphorus atom, with at least one tetravalent metal ion selected from the group consisting of zirconium, thorium, cerium, uranium, lead, hafnium and titanium to form a solid inorganic polymer precipitate in which phosphorus is linked to the metal by oxygen and the organo group is covalently bonded to the phosphorus atom. Where, in the organophosphorus compound, n is 2, the end product occurs in the bis configuration. In this configuration, R must contain two or more carbon atoms, preferably from two to about twenty carbon atoms, such that at least two carbon atoms separate the phosphorus atoms. In this bis configuration no single carbon atom is bound directly or indirectly to more than one [PO(OH)$_2$] group. When n is 1, and as depicted in FIG. 7, the organo groups will be pendant from phosphorus atoms. When n is 2, and as depicted in FIG. 8, cross-linking will occur between interlamellar surfaces of the crystalline end product. Typically, the tetravalent metal ion is provided as a soluble salt MX wherein M is as defined above and X is the anion(s) of the salt. The typical anions include halides, $HSO_4^{-1}$, $SO_4^{-2}$, $O_2C-CH_3^{-1}$, $NO_3^{-1}$, $O^{-2}$ and the like.

The majority of the polymeric reaction products formed are found to be layered crystalline or semi-crystalline in nature and, as such, provided layered structures similar to zirconium phosphates. The remainder are amorphous polymers possessing a large quantity of available pendant groups similar to silica gel.

By the term "organophosphorus acid compound", as used herein, there is meant a compound of the formula:

$$[(HO)_2OP]_nR$$

wherein n is 1 or 2, R is any group which will replace a hydroxyl of phosphoric acid and/or the hydrogen of phosphorous acid and couple to the acid by a covalent bond. Coupling of the acid may be through carbon, oxygen, silicon, sulfur, nitrogen and the like. Coupling through carbon or an oxygen-carbon group is presently preferred.

When, in the organophosphorus compound, n is 2, the end product occurs in the bis configuration. In this configuration, R must contain three or more carbon atoms, preferably from two to about twenty-six carbon atoms, such that at least two carbon atoms separate the phosphorus atoms. In this bis configuration, no single carbon atom is bound directly or indirectly to more than one [PO(OH)$_2$] group. Thus the groups which link to the metal have the basic structural formula:

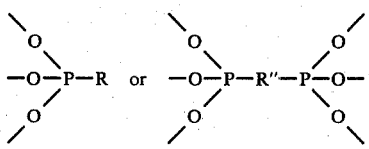

wherein R" is a bis group containing at least two carbon atoms bonded directly or indirectly to phosphorus, such that no phosphorus atoms are bonded directly or indirectly to the same carbon atom. The basic structures of the inorganic polymer forms are shown in FIGS. 7 and 8.

When coupling is through carbon, the organo phosphorus acid compound is an organo phosphonic acid and the product a phosphonate. When coupling is through oxygen-carbon, the organophosphorus acid compound is an organo-phosphoric monoester acid and the product a phosphate.

The general reaction for phosphonic acids alone is shown in equation (1) below and for monoesters of phosphoric acid alone by equation (2).

$$M^{+4} + 2(HO)_2OPR \rightarrow M(O_3P-R)_2 + 4H^+ \quad (1)$$

$$M^{+4}+2(HO)_2OP-OR' \rightarrow M(O_3P-OR')_2+4H^+ \quad (2)$$

wherein R' is the remainder of the organo group.

The product contains phosphorus to metal in a molar ratio of about 2 to 1, and the empirical formula for the product would show all organo groups bond to phosphorus.

While nowise limiting, the R groups attachable to phosphorus may be saturated and unsaturated, substituted and unsubstituted and include, among others, alkylene, alkyloxy, alkyne, aryl, haloalkyl, alkylaryl, aryloxy, mercaptoalkyl, aminoalkyl, carboxyalkyl, morpholinoalkyl, sulfoalkyl, phenoxyalkyl, beta-diketo alkyl, cyanoalkyl, cyanoalkoxy, heterocyclics and the like.

In general, the organo group should occupy no more than about 25 Å² for proper spacing. This limitation is imposed by the basic crystal structure of zirconium phosphate. Referring to FIG. 4, a spacing of 5.3 Å is shown between zirconium atoms in the zirconium plane of a crystal a total area of about 24 Å² is shown for the space bounded by zirconium atoms. It follows that any group anchored on each available site cannot have an area much larger than the site area and maintain the layered structure.

This limitation can be avoided through the use of a combination of larger and smaller groups, i.e., mixed components. If some of the sites are occupied by groups which have an area much less than about 24 Å², adjacent groups may be somewhat larger than 24 Å² and still maintain the layered structure of the compound.

The cross-sectional area which will be occupied by a given organo group can be estimated in advance of actual compound preparation by use of CPK space filling molecular models (Ealing Company) as follows: A model of the alkyl or aryl chain and terminal group is constructed, and it is situated on a scaled pattern of a hexagonal array with 5.3 Å site distances. The area of the group is the projection area on this plane. Some areas which have been determined by this procedure are listed in Table 1.

TABLE 1

| Moiety | Minimum Area (Å²) | Moiety | Minimum Area (Å²) |
|---|---|---|---|
| Alkyl chain | 15 | Isopropyl | 22.5 |
| Phenyl | 18 | t-butyl | 25 |
| Carboxyl | 15 | Chloromethyl | 14 |
| Sulfonate | 24 | Bromoethyl | 17 |
| Nitrile | 9 | Diphenylphosphine | 50 (approx.) |
| Morpholinomethyl | 21 | Mercaptoethyl | 13.5 |
| Trimethylamino | 25 | | |

The process for the formation of the novel inorganic polymers is a metathesis reaction conducted in the presence of a liquid medium receptive to the tetravalent metal ion at a temperature up to the boiling point of the liquid medium, preferably from ambient to about 150° C. and, more preferably, to about 100° C. at the pressure employed.

While water is the preferred liquid medium, as most of the organophosphorus acid compounds are water soluble, an organic solvent such as ethanol may be employed, where water interferes with the reaction. There need only to be provided a solvent for the organophosphorus acid compound since the tetravalent ion can be dispersed as a solid in the solvent for slow release of the metal ion for reaction with the organophosphorus acid compound. If it has a sufficiently low melting point, the organophosphorus acid compound may serve as a solvent. Typically, the liquid medium is the liquid medium in which the organophosphorus acid is formed.

For complete consumption of the tetravalent compound, the amount of acid employed should be sufficient to provide two moles of phosphorus per mole of tetravalent metal. An excess is preferred. Phosphorous acid and/or phosphoric acid, if present, will enter into the reacton and provide an inorganic polymer diluted in respect to the organo group in proportion to the amount of phosphorous or phosphoric acid employed.

Reaction is virtually instantaneous at all temperatures leading to precipitation of layered crystalline, semi-crystalline or amorphous inorganic polymer solid.

The amorphous phase appears as a gel similar to silica gel. The gel can be crystallized by extended reflux in the reaction medium, usually from about 5 to about 15 hours. The semi-crystalline product is characterized by a rather broad X-ray powder diffraction pattern.

The presence of sequestering agents for the metal ion slows down the reaction and also leads to more highly crystalline products. For instance, a semi-crystalline solid has been prepared by the aqueous phase reaction of zirconium oxychloride and excess 2-carboxyethyl phosphonic acid, followed by 15 hours of reflux. A highly crystalline modification was prepared under identical conditions except that hydrogen fluoride was added to the reaction mixture. A slow purge of N₂ over the surface of the reaction solution slowly removed the fluoride from the system. Fluoride is a very strong complexing agent for zirconium ions. The slow removal of fluoride results in slow release of the metal ion for reaction with the phosphonic acid, resulting in an increase in crystallinity.

A similar enhancement of crystallinity was obtained in the reaction of thorium nitrate with 2-carboxyethyl phosphonic acid. Nitrate ion is a sequestering agent for thorium and the rate of formation of this product is slow and the product polymer quite crystalline.

As compared to zirconium phosphate forming crystals of 1-5 microns, the crystals of 100 to greater than 1000 micron in size have been prepared in accordance with the invention.

A property critical for many of the likely uses of the products is their thermal stability. This is because deficiencies in activity can be compensated for by reasonable increases in operating temperature. A standard method for thermal characterization is thermal gravimetric/differential thermal analysis (TGA/DTA). These techniques indicate changes in weight and heat flow of substances as a function of temperature. Thus, decomposition and phase changes can be monitored as temperature increases.

Zirconium phosphate itself is quite a stable material. Interlayer water is lost at about 100° C., and a second dehydration involving the phosphates occurs above 400° C. The practical ion-exchanging abilities are lost in this step.

The inorganic polymers of this invention are also stabilized toward thermal decomposition as compared to pure organic analogs as a result of the fixation and separating effect of the inorganic support.

For zirconium chloromethyl phosphonate, for instance, weight loss did not commence until well above 400° C. The organic fragment was half lost at about 525°

C., indicating remarkable stability. Decomposition of zirconium 2-carboxyethylphosphonate begins between 300° and 400° C. The decomposition process inflection point, approximate mid-point, falls at about 400° C.

While not bound by theory, phosphates probably decompose like carboxylic esters to yield acid and unsaturates, whereas phosphonates likely form radicals by homolytic cleavage. Both nitrophenyl and cyanoethyl phosphates of zirconium decompose at about 300° C. The phenylphosphonate decomposes at about 425° C.

Besides proving the suitability of such compounds in elevated temperature applications, the TGA analysis affirmed covalent bonding to phosphorous. This is because normal intercalative interactions are reversed within 10° to 100° C. above the boiling point of the guest.

The process disclosed herein permits a wide variety of inorganic polymers to be formed having the characteristic of the organo group protected by the inorganic polymer structure and, with subsequent exchange or substitution reactions, the formation of other inorganic polymers. Polymers formed may be block, random and the like.

For instance, a mixture of phenyl phosphonic acid and phosphorous acid was simultaneously reacted with zirconium ion to yield a single solid phase. The interlamellar distance was the same as zirconium phenyl phosphonate, or about 15.7 Å. There was no reflection at 5.6 Å, the normal spacing for zirconium phosphite. This established that the largest group should determine interlamellar distance and indicated that a discreet zirconium phosphite phase was not present. Evidence of a change in chemical environment of P-H band was established by infrared analysis. In infrared analysis of zirconium phosphite, P-H stretching is observed as a sharp band at 2470 cm$^{-1}$ (moderate intensity). In the mixed compound solid, this band was shifted to 2440 cm$^{-1}$ and broadened.

Another route is to exchange one pendant group for another. While not bound by theory, the present expected points of exchange are at the periphery of the crystal and are schematically illustrated in FIG. 6. Such bifunctional materials exhibit the quality of providing terminal groups for attracting species for intercalation and then interaction with the internal groups.

The reaction of bis acids with tetravalent metal ions permits interlamellar cross-linking by a reaction such as $(HO)_2OPCH_2CH_2OP(OH)_2 + M^{+4} \longrightarrow \underset{\bot\bot\bot\bot\bot\bot}{\vdash}-CH_2CH_2-\underset{\bot\bot\bot\bot\bot\bot}{\dashv}$ where as in FIG. 6, ⊥⊥⊥⊥⊥⊥ represents the interlamellar layer to which the alkyl group is anchored. As with all organo groups, for the bis configuration at least two carbon atoms are present, preferably from two to twenty atoms, and the phoshorus atoms are linked directly or indirectly to different carbon atoms. Since size of the linking group will control and fix interlamellar spacing, there is provided effective laminar sieves of fixed spacing for application analogous to that of molecular sieves.

Ion exchange activity as been established with pendant carboxylic acid groups. Prepared zirconium 2-carboxyethyl phosphonate was established to have an interlayer distance of 12.8 Å. When intercalated to form its n-hexylammonium salt interlayer distance increased to 27.2 Å. When sodium was taken up, layer spacing increased to 14.2 Å. X-ray and infrared data indicated the highly crystalline inorganic polymer to behave as expected for carboxylic acid with behavior analogous to ion exchange resins except that both external and internal surfaces were functional establishing them as super surface ion exchange resins. Moreover, since the inorganic polymers can be prepared as microcrystalline powders, diffusion distances are short.

As summarized in Table II, nitrile and mercapto anchored groups show the ability to take up silver and copper ions at room temperature for catalytic activity.

TABLE II

| Anchored Group | Metal Ion | Loading $\frac{\text{mMole Metal}}{\text{mMole Zr}}$ |
|---|---|---|
| —O CN | 0.1 M Ag$^+$ | 0.20 |
| SH | 0.1 M Ag$^+$ | 1.00 |
| —O CN | 0.1 M Cu$^{++}$ | 0.10 |
| —O CN | 0.1 M Cu$^{++}$ 0.5 M HOAc 0.5 M NaOAc | 0.10 |

—O = groups formed of carbon and hydrogen.
OAc = acetate radical.

OAc = acetate radical.

The alternate to catalytic utility is to attach the metals to the organophosphorus acid prior to reaction with the soluble tetravalent metal compound.

The high surface area of the crystalline products also make them utile for sorption of impurities from aqueous and non-aqueous media.

Another utility is as an additive to the polymeric compositions. Similar to the high aspect ratio provided by solids such as mica which improve the stress strain properties of the polymers, the powdered inorganic polymer products of the invention can serve the same function and add features. By the presence of reactive end groups on the bonded organo groups, chemical grafting to the polymer network can be achieved to increase composite crystallinity and elevating heat distortion temperature. In addition, the presence of phosphorus induces flame retardant properties, as would bound halogen.

Still other utilities include solid lubricants which behave like mica, graphite and molybdenum disulfide; solid slow release agents where intercalated materials can be slowly leached or released from the internal layers of the crystals, substances displaying electrical, optical, phase or field changes with or without doping and the like.

While nowise limiting, the following Examples are illustrative of the preparation of solid inorganic polymers of this invention and some of their utilities.

In the Examples conducted in the atmosphere no extraordinary precautions were taken concerning oxygen or moisture. Reagents were usually used as received from suppliers. The products formed are insoluble in normal solvents and do not sublime. However, the combined weight of yield data, spectroscopy, elemental analyses and powder diffraction results confirm the compositions reported with good reliability.

EXAMPLE I

Preparation of:

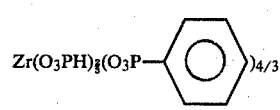

In a reaction flask was added an aqueous solution which had been formulated by dissolving 2.004 g of ZrOCl$_2$.8H$_2$O in water which had been deoxygenated by bubbling in nitrogen gas therethrough. The reaction flask was then blanketed with an inert atmosphere of nitrogen and the solution was mixed with a solution containing 3.086 g of a 30% by weight $H_3PO_3$, 1.778 g phenyl phosphonic acid and one ml of hydrochloric acid. Deoxygenated water was added to bring the total volume to about 75 ml.

The resulting mixture was heated until it started to exhibit refluxing. A solid precipitate appeared. The mixture was then divided into two equal portions. The first portion was filtered and the separated precipitate was washed with successive washes of water and acetone. This first precipitate was dried at about 80° C. The second portion of the mixture was heated and refluxed under nitrogen atmosphere for about 24 hours. Following refluxing the second portion of the mixture was filtered to separate the second precipitate from the liquid. The recovered second precipitate was washed successively with water and acetone and dried at about 80° C. for a few hours.

The first precipitate recovered from the first portion of the mixture weighed about 0.728 g and the second precipitate recovered from the refluxed second portion weighed about 2.156 g. The total combined weight of the recovered precipitates, $Zr(PO_3H)_{2/3}$ $(PO_3\text{—}\langle\bigcirc\rangle)_{4/3}$ was 2.884 g.

Elemental analysis of the recovered first product provided the following results: 25.05% C and 2.86% H. An X-ray powder diffraction pattern showed the compound to be amorphous. Elemental analysis of the recovered second product provided the following results: 27.22% C and 2.88% H. An X-ray powder diffraction pattern showed the second compound to be semicrystalline having an interlayer spacing of 15.8 Å. Infrared analysis of the present showed both the P-H stretch at 2440 cm$^{-1}$ and benzene absorptions at 700, 740 and 760 cm$^{-1}$.

EXAMPLE II

Preparation of: $Zr(O_3POH)_{2/3}(O_3PCH_2CH\text{=}CH_2)_{4/3}$

In a 125 ml Erlenmeyer flask was reacted 9.900 g of $(EtO)_2PCH_2CH\text{=}CH_2$
             ‖
             O and 36 g (about a two-fold excess of 48% HBr solution. The reaction mixture was refluxed for about 45 minutes. During refluxing ethyl bromide was collected. The refluxed liquid contained $(HO)_2\text{—}PCH_2CH\text{=}CH_2$.
          ‖
          O About 0.0139 moles of the $(HO)_2\text{—}PCH_2CH\text{=}CH_2$
          ‖
          O was mixed with 0.0070 moles of $(HO)_2\text{—}POH$
          ‖
          O (about 0.805 g of an 85% $H_3PO_4$, water and about 20 ml THF.

The solution was thoroughly intermixed and reacted with an aqueous solution containing 1.846 g $ZrOCl_2$. A precipitate formed immediately upon mixing. The reaction mixture was refluxed for about one hour and heating was continued below refluxing conditions for overnight.

The reaction mixture was cooled to room temperature and filtered. The white, solid precipitate collected $Zr(O_3POH)_{2/3}(O_3PCH_2CH\text{=}CH_2)_{4/3}$ was washed with successive washes of water, acetone and ether. The solid was then dried at a temperature of about 90° to 100° C. for about one hour. The amount of solid collected was 2.645 g which was about an 81% yield from a theoretical value of 3.269 g.

Upon infrared analysis the solid precipitate exhibited a characteristic C=C stretching at 1650 cm$^{-1}$.

Elemental analysis of the recovered product provided the following resuls: 15.40% C and 3.13% H. An X-ray powder diffraction pattern showed the compound to be amorphous.

EXAMPLE III

Preparation of:

$Zr\left[O_3P\text{—}O\text{—}\langle\bigcirc\bigcirc\rangle\right]_{1.0}(O_3POH)_{1.0}$ In a reaction vessel was added 1.000 g of $HO\text{—}P\text{—}O\text{—}\langle\bigcirc\bigcirc\rangle \cdot 1H_2O$
       ‖
       O
       |
     Na\text{—}O which was dissolved in methanol. Added to the flask was about 0.200 g of a 98% solution of sulfuric acid mixed with methanol. The sulfuric acid provided the phosphonic acid produced from the sodium salt. The phosphonic acid was produced and sodium sulfate was precipitated from the methanol. The sodium sulfate was removed by filtering.

Into the methanol solution containing the phosphonic acid was added 0.619 g of $Zr(OC_3H_7)_4$ and about 20 drops of a 30% solution of hydrofluoric acid. The hydrofluoric acid was added to assist in crystallizing the product.

The mixture was then heated under reflux conditions for about five hours. Following reflux the mixture was cooled to room temperature and filtered to separate the solid precipitate formed. The precipitate was washed with acetone, air dried and oven dried at about 70° C. for about one hour. The amount of

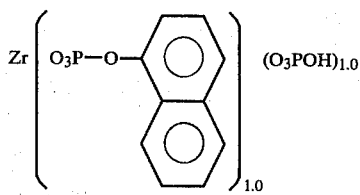

recovered was 0.651 g.

Elemental analysis of the recovered product provided the following results: 27.08% C and 1.88 H. An X-ray powder diffraction pattern showed the compound to be crystalline, having an interlayer spacing of 18.2 Å.

This is an example of a mixed component product formed by partial hydrolysis of the starting phosphate, rather than admixture of two monomeric phosphorous dianions. When

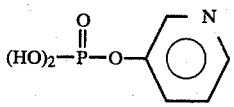

(pyridyl-3-phosphoric acid) was the starting material, the same process occurred, partial hydrolysis to form a mixed product,

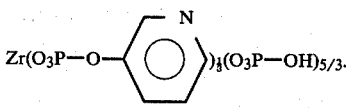

EXAMPLE IV

Preparation of: $Zr(O_3P(CH_2)_{10}PO_3)_{1/3}(O_3POH)_{2/3}$

A stock solution of bisphosphonic acid was prepared by reacting 15.05 g of

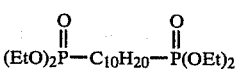

with 32 ml of 48% solution of hydrogen bromide. The hydrogen bromide was present in about 100% excess. The two solutions were mixed and heated to reflux in a round bottom flask fitted with a Dean-Stark trap for collecting ethyl bromide and a condenser. After about 15 hours of vigorous refluxing the reaction was about 90% complete as evidenced by the collected ethyl bromide. The reflux liquid provided in the stock solution of bisphosphonic acid

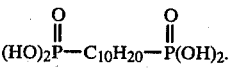

A solution was prepared by dissolving 1.92 g of $ZrOCl_2$ (10.8 mM) in ten ml of water and 40 ml of methanol. To this solution was added 25 ml of the stock solution of bisphosphonic acid (3.6 mM) to which had been added 1.66 grams of 85% phosphoric acid (14.10 mM).

The reaction mixture was then refluxed for about two and one-half hours. The mixture was then filtered to separate the formed precipitate. The precipitate was air dried to a weight of about 5.9 g. The precipitate was then dried at about 60° C. for three hours whereupon it turned yellow and had a weight of 3.28 g.

Elemental analysis of the recovered product provided the following results: 13.95% C and 4.06 H. An X-ray powder diffraction pattern showed the compound to be semicrystalline having an interlayer spacing of 17.3 Å.

EXAMPLE V

Preparation of: $Zr(O_3POCH_2CH_2CN)_{2/3}(O_3PH)_{4/3}$

A solution of 3.27 g $BaPO_4CH_2CH_2CN$ (10 mM) and 2.75 g of a 30% $H_3PO_3$ solution and one ml of hydrochloric acid was diluted to about 30 ml. To the solution was added about 20 ml of an aqueous solution containing 1.353 g $ZrOCl_2$ (7.5 mM).

Upon the addition and mixing of the solutions a white gelatinous precipitate was formed. The reaction mixture was refluxed about one hour. Following refluxing the precipitate solid was separated by filtration. The solid separated was washed with methanol and acetone and allowed to air dry yielding 1.984 g of the solid.

Upon infrared analysis of the precipitate, both the CN and P-H bond stretching characteristic peaks were observed.

EXAMPLE VI

Preparation of: $Zr(O_3PCH_2CH_2P\phi_2)_{2/3}(O_3PCH_3)_{4/3}$

Into a suitable reaction flask was added 0.810 g of an aqueous solution of 85% by weight

(0.689 g) dissolved in about 100 ml of methanol. The reaction was conducted under an inert atmosphere of nitrogen. A solution of 0.22 g of $ZrOCl_2$ was dissolved in about 2 ml water. This solution was added to the reaction flask with stirring. No precipitate appeared.

The resulting solution was heated to cause refluxing of the solution for about one hour. No precipitate was formed upon refluxing. To the refluxing solution was added 0.405 g of $ZrOCl_2$. A methanol solution containing 0.4050 g of

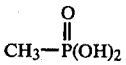

was also added to the refluxing solution.

After 30 seconds of adding the

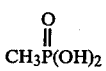

a haze appeared which slowly thickened into a gel. With continued refluxing the gel became a solid and exhibited particle-like properties. The reaction mixture was refluxed for about 5 hours and allowed to cool. The mixture was then filtered under a nitrogen atmosphere to separate the precipitate from the liquid. The recovered solid was washed with methanol and dried under nitrogen at room temperature over night. The solid recovered was orange in color. The particles were clear and averaged about 0.55 mm in diameter. The recovered solid Zr(O₃PCH₂CH₂Pθ₂)₂/₃(O₃PCH₃)₄/₃ weighed 1.230 g.

EXAMPLE VII

Preparation of:
Zr(O₃PCH₂CH₂CH₂Pθ₂)₀.₄(O₃PCH₃)₁.₆

In a reaction vessel was dissolved 2.31 g (7.5 mM) of

(HO)₂PCH₂CH₂CH₂Pφ₂ in ethanol. Mixed with the ethanol solution was 1.95 g (11.4 mM) of CH₃P(OH)₂.

A solution of 1.700 g of ZrOCl₂ dissolved in water was added to the above solution of phosphonic acid. A slight excess of ZrOCl₂ was used as the stoichiometric amount was 1.683 g.

A light yellow precipitate formed immediately upon the addition and mixing of the two solutions. The mixture was heated to about 60° C. over a weekend.

The light yellow precipitate was separated from the supernatant liquid by filtration after cooling the mixture to room temperature. The recovered solid was washed with ethanol and ether and allowed to air dry. The filtrate washed through the filter with a yellow color. After about five hours of air drying the solid Zr(O₃PCH₂CH₂CH₂Pθ₂)₀.₄ (O₃PCH₃)₁.₆ recovered weighed about 3.605 grams.

Both products of Examples VI and VII were found to swell and incorporate Pd(II) when contacted with solutions of Pd(Cl)₂(CH₃CN)₂.

EXAMPLE VIII

Preparation of: Zr(O₃PCH₂Cl)₄/₃(O₃POH)₂/₃

A solution of 10 ml 3.9 M solution of

(HO)₂PCH₂Cl (39 mM) and 4.5 g H₃PO₄ (39 mM) was diluted to about 25 ml. To the diluted solution was added a solution of 4.5 g ZrOCl₂ (25 mmol) in 20 ml of water.

A dense white precipitate formed which was substantially redissolved by the addition of about 5 ml HF solution. The reaction mixture was refluxed for about 2 hours. During refluxing the mixture cleared and after additional refluxing a precipitate reappeared. The reaction mixture was cooled and filtered to recover the precipitate which weight 6.75 g after air drying over night.

Upon analysis of the precipitate it was determined that the precipitate was Zr(O₃PCH₂Cl)₄/₃(O₃POH)₂/₃.

EXAMPLE IX

Preparation of:

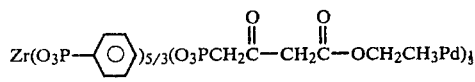
Zr(O₃P—⟨O⟩)₅/₃(O₃PCH₂C(O)—CH₂C(O)—OCH₂CH₃Pd)₁

Into a reaction flask was charged 6.748 g of

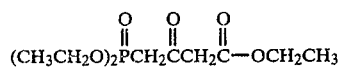
(CH₃CH₂O)₂PCH₂CCH₂C—OCH₂CH₃

(0.0298 moles). A hydrochloric acid solution was prepared having a pH of about 2. Palladium chloride (PdCl₂), 2.638 g, was dissolved in 50 ml of the hydrochloric acid solution. The acidic palladium chloride solution was then poured into the flask containing the phosphonate. The palladium chloride solution was brown and it was apparent that much of the solution remained in the beaker in which it was mixed. The beaker was then washed with additional hydrochloric acid solution until all of the palladium chloride had been transferred to the reaction flask. The total volume of the reaction mixture in the flask was about 125 ml. The reaction flask was fitted with a condenser and magnetic stirrer. The reaction mixture was heated to reflux. Upon initiating refluxing, the palladium chloride appeared to be dissolved and the solution was a dark brown. None of the palladium chloride could be seen on the bottom of the flask. About about one hour of heating the reaction mixture was filtered hot through a fritted disk. The filtrate recovered was a red-brown color and a black solid was left on the filter. The filtrate was filtered a second time and a very light black solid was recovered on the filter.

The hot filtrate was cooled to 40° C. and 1.178 g of phenyl phosphonic acid,

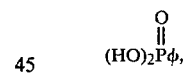
(HO)₂Pφ, was added. The filtrate was a dark color but free of suspended solids before and after the addition of the phenol phosphonic acid.

The filtrate was transferred to a two-neck flask. To the flask was then added in 2 to 3 ml increments a solution of 14.418 g of ZrOCl₂.8H₂O dissolved in 10 ml of water. An immediate tan precipitate was formed after the addition of the first increment. After all of the ZrOCl₂ solution had been added, the mixture was stirred and heated with a heating mantle to reflux the reaction mixture overnight.

The black solid collected after separating the filtrate contained 1.15 g of palladium.

Following refluxing the reaction mixture, the reaction mixture was filtered to collect the precipitate which had formed during the refluxing.

The precipitate was initially a grey crystalline material in appearance. The precipitate was washed with successive washes of water, acetone and ether and dried under a vacuum for one hour. The amount of product recovered was 4.56 g which was about a 24% yield.

EXAMPLE X

The mixed component product of Example IV was shown to be very selective in its complexative absorption of amines by virtue of the ten carbon cross-links from one layer to the next. This behavior is a form of "molecular sieving."

In four separate experiments the behavior of two —OH containing zirconium phosphate layered solid toward two different amines was investigated. The two amines were a bulky trioctylamine and a small ethylamine. As the table below indicates, the noncross-linked zirconium phosphate picked up both amines from a methanolic solution. However, the product of Example IV picked up only the small amine, due to the constricting effect of the bridging ten carbon group.

TABLE
ABSORPTION OF AMINES

| Solid | Amine | Molar Ratio of Amine/—OH Group in Product |
|---|---|---|
| $Zr(O_3P-OH)_2$ | $C_2H_5NH_2$ | 0.86 |
| $Zr(O_3P-OH)_2$ | $(C_8H_{17})_3N$ | 0.24 |
| $Zr(O_3P(CH_2)_{10}PO_3)_{\frac{1}{3}}(O_3POH)_{4/3}$ | $C_2H_5NH_2$ | 0.31 |
| $Zr(O_3P(CH_2)_{10}PO_3)_{\frac{1}{3}}(O_3POH)_{4/3}$ | $(C_8H_{17})_3N$ | 0.00 |

EXAMPLE XI

Preparation of: $Zr(O_3P\theta)_{8/5}(O_3PCH_2CH_2CO_2H)_{2/5}$

To a 500 ml round bottom reaction flask fitted with an addition funnel, mechanical stirrer, thermometer, reflux condenser and heating mantle was charged an aqueous solution containing 4.0 g of 2-carboxyethylphosphonic acid (0.026 mole) and an aqueous solution containing 16.4 g of phenylphosphonic acid (0.104 mole). To the addition funnel was charged 11.56 g of $ZrOCl_2$ (0.064 mole) dissolved in a minimum amount of water. The phosphonic acids solution was heated to about 50° C. and the $ZrOCl_2$ solution added dropwise. The product formed as a white precipitate and was refluxed over the weekend. The reaction mixture was cooled and the product isolated by filtration and washed successively with acetone and ethyl ether. After oven drying, the white product weighed 20.4 g.

EXAMPLE XII

Extraction of palladium +2 ion from aqueous solution by ion exchange with $Zr(O_3P\theta)_{8/5}(O_3PCH_2CH_2CO_2H)_{2/5}$.

A solution of palladium(II)chloride was prepared by dissolving about 1.0 g of commercially available palladium(II)chloride in about 100 ml of water under a nitrogen purge. A small amount of undissolved material was removed by filtration. The pH of this solution was 2.90. To this solution was added 3.0 g of $Zr(O_3P\theta)_{8/}$. $_5(O_3PCH_2CH_2CO_2H)_{2/5}$. The pH decreased to 2.35. Using an auto-titrator in a pH stat mode, the pH was raised in small steps to 3.5 by addition of 0.10 N aqueous sodium hydroxide. The pale yellow solid product was isolated by filtration and washed successively with water, acetone and ethyl ether. After oven drying, elemental analysis indicated 3.72% Pd content of the solid phase.

This example demonstrates the extraction of a precious metal, more broadly a Group VIII metal, from solution. The palladium containing product now incorporates a catalytically active species and represents a novel example of a heterogenized or anchored catalyst which can be used for the reactions shown in the J. C. Bailar and Hartley & Vezey publications incorporated herein.

Similarly, the compounds in the previous examples can be useful as catalysts, especially when a catalytically active Group VIII metal (e.g., Pt, Pd, Rh, Ru, etc.) is incorporated into the compound, e.g., by intercalation, ion exchange, complexation or impregnation by techniques described herein or those well known in the art of catalysis.

Other metal $^{+4}$ ions which are analogous to $Zr^{+4}$ in the process to make phosphate and phosphonate analogs, are metals with approximately the same ionic radius as $Zr^{+4}$ (0.8 Å), for example,

| $Zr^{+4}$ | 0.80Å | $Te^{+4}$ 0.81 | $Pr^{+4}$ 0.94 | $Mn^{+4}$ 0.5 |
|---|---|---|---|---|
| $W^{+4}$ | 0.66 | $Sn^{+4}$ 0.71 | $Pb^{+4}$ 0.92 | $Ir^{+4}$ 0.66 |
| $U^{+4}$ | 0.89 | $Si^{+4}$ 0.41 | $Os^{+4}$ 0.67 | $Hf^{+4}$ 0.81 |
| $Ti^{+4}$ | 0.68 | $Ru^{+4}$ 0.65 | $Nb^{+4}$ 0.67 | $Ge^{+4}$ 0.53 |
| $Th^{+4}$ | 0.95 | $Pu^{+4}$ 0.86 | $Mo^{+4}$ 0.68 | $Ce^{+4}$ 1.01 |

The thio analogs of the phosphonates and phosphates can also be made by this process. The larger, more readily redoxable elements can lead to semiconducting, photoactive supports. All of the above noted solid, layered compounds can be useful as a chromatographic solid phase, adsorbants ion-exchange and hosts or carriers for controlled release of active substances.

In the preparation of anchorable Layered Compounds, a general approach to zirconium phosphate and the other zirconium compositions described herein and in the applications incorporated herein involve the following concepts:

(1) Tetrahedral anions with 3-metal coordinating groups and one interlayer group desirable

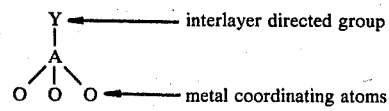

(2) Charge on anion should be −1, −2, −3 (charge on metal ion therefore should be +2, +4, +6 for M[O-$_3$AY]$_2$ stoichiometry needed for sandwiching and bridging configuration)

(i) for −1 charge, conjugate acid of anion

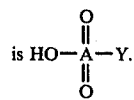

"A" can be S (or Se, Cr, Mo, W, etc., (+6 forming elements)

(ii) for −2 charge, conjugate acid of anion

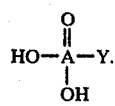

"A" can be P, As, Sb, V, Nb, Ta, etc., (+5 forming elements)

(iii) for −3 charge, conjugate acid of anion is HO—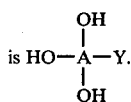Y.

"A" can be Si, Ge, Ti, Zr, Sn, Pb (+4 forming elements).

Some exemplary salts which meet these criteria are listed below.

M[O₃A—Y]₂: Examples of compounds of structure which can form layered host structures analogous to zirconium phosphate and the phosphorous or arsenic containing compounds of the applications incorporated herein:

(1) [O₃A—Y]⁻¹ A=S, for example, Y=NH₂ (conjugate acid is sulfamic acid)
M+ = $Cu^{+2}$, $Zn^{+2}$, $Fe^{+2}$, alkaline earths

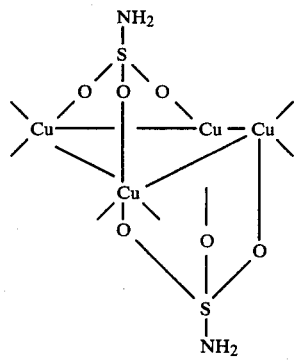

(2) [O₃A—Y]⁻² — Zirconium phosphate prototypes (A=P, As, Sb, etc.)
(3) [O₃A—Y]⁻³ — A=Si, for example, Y=OCH₂CN, M=Mo⁺⁶

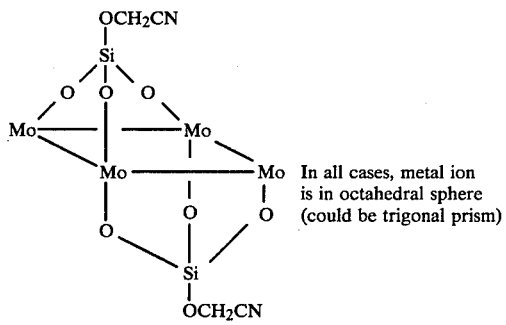

In all cases, metal ion is in octahedral sphere (could be trigonal prism).

Although the structure of these solid phases is polymeric in nature, it is convention in solid inorganic nomenclature to refer to them by their monomeric units.

Redox catalysts can be obtained when the solid inorganic polymer (e.g., organophosphorus) contains an organo-group of the quinone-hydroquinone type.

What is claimed is:

1. A process for the production of phosphorus-containing organo-substituted inorganic polymers containing multi-component derivatized groups, which comprises reacting
   (a) at least one species of tetravalent metal ion in a liquid medium with at least two members selected from phosphoric acid, phosphonic acid and organophosphorus acids of the formula:

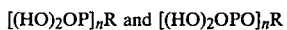

wherein n is 1 or 2 and R is an organo group covalently coupled to phosphorus and wherein when n is 2, R contains at least two carbon atoms and is directly or indirectly coupled to the phosphorus atoms through different carbon atoms whereby the two phosphorus atoms are separated by at least two carbon atoms, and
   (b) causing precipitation from the liquid medium of a solid inorganic polymer in which the molar ratio of phosphorus to tetravalent metal is about 2 to 1 and in which the organo group is covalently bonded to phosphorus and phosphorus is linked to the tetravalent metal through oxygen.

2. The process of claim 1 in which the liquid medium comprises water.
3. A product of the process of claim 1.
4. The process of claim 1 wherein said tetravalent metal comprises zirconium.
5. The process of claim 1 wherein one of said members comprises phosphonic acid.
6. The process of claim 1 wherein one of said members comprises phenyl phosphonic acid.
7. The process of claim 6 wherein the other member comprises phosphonic acid and the tetravalent metal ion comprises zirconium.
8. A solid polymer product of the process of claim 4.
9. A solid polymer product of the process of claim 5.
10. A solid polymer product of the process of claim 6.
11. An amorphous solid polymer product of the process of claim 7.
12. A semi-crystalline polymer product of the process of claim 7.
13. The process of claim 1 wherein at least one said member contains a phosphine group.
14. A solid polymer product of claim 13.
15. The process of claim 13 wherein said members comprise 2-(diphenyl phosphino)-ethyl phosphonic acid and methyl phosphonic acid.
16. A solid polymer product of the process of claim 15.
17. The process of claim 13 wherein said members comprise 3-(diphenyl phosphino)-propyl phosphoric acid and methyl phosphonic acid.
18. A solid polymer product of claim 17.
19. A process for the production of phosphorus-containing organo-substituted layered inorganic polymers containing multi-component derivatized groups, which comprises reacting in a liquid medium:
    (a) at least one species of tetravalent metal ion;
    (b) with at least two members selected from phosphoric acid, phosphonic acid and organophosphorus acids of the formula:

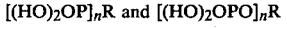

wherein n is 1 or 2 and R is an organo group covalently coupled to phosphorus and wherein when n is 2, R contains at least two carbon atoms and is directly or indirectly coupled to the phosphorus atoms through different carbon atoms whereby the two phosphorus atoms are separated by at least two carbon atoms,
    for precipitating from the liquid medium, a solid comprising layered inorganic polymers in which inorganic polymers the molar ratio of phosphorus to tetravalent metal is about 2 to 1, the organo group is covalently bonded to phosphorus, and phosphorus is linked to the tetravalent metal through oxygen.

20. A process for the production of phosphorus-containing organo-substituted inorganic polymers containing multi-component derivatized groups, which comprises reacting in a liquid medium:

(a) at least one species of tetravalent metal ion;
(b) with at least two members selected from phosphoric acid, phosphonic acid and organophosphorus acids of the formula:

$$[(HO)_2OP]_nR \text{ and } [(HO)_2OPO]_nR$$

wherein n is 1 or 2 and R is an organo group covalently coupled to phosphorus and wherein when n is 2, R contains at least two-carbon atoms and is directly or indirectly coupled to the phosphorus atoms through different carbon atoms whereby the two phosphorus atoms are separated by at least two carbon atoms, for precipitating from the liquid medium, a solid comprising spaced apart sheets of inorganic polymers in which inorganic polymers the molar ratio of phosphorus to tetravalent metal is about 2 to 1, the organo group is covalently bonded to phosphorus, and phosphorus is linked to the tetravalent metal through oxygen.

21. A phosphorus-containing organo-substituted inorganic polymer containing multicomponent derivatized groups and including structural units having the empirical formula:

$$M(O_3PZ)_x(O_3PO_nR)_y$$

wherein n is 0 or 1, x+y=2, Z is selected from the group consisting of H, OH, and R, R is an organo group covalently coupled to phosphorus, M is a tetravalent metal structurally linked to phosphorus through oxygen and wherein the molar ratio of phosphorus to tetravalent metal is about 2 to 1.

22. A phosphorus-containing organo-substituted inorganic polymer containing multicomponent derivatized groups and including structural units having the empirical formula:

$$M(O_3PZ)_x(O_3PO_nRO_nPO_3)_y$$

wherein n is 0 or 1, x+y=1, Z is selected from the group consisting of H, OH and R, R is an organo group comprising at least two carbon atoms and is directly or indirectly coupled to the phosphorus atoms through different carbon atoms whereby the phosphorus atoms are separated by at least two carbon atoms, M is a tetravalent metal structurally linked to phosphorus through oxygen and wherein the molar ratio of phosphorus to tetravalent metal is about 2 to 1.

23. An inorganic polymer as recited in claim 21 having empirical structural units of the formula:

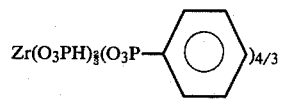

24. An inorganic polymer as recited in claim 21 having the empirical formula:

$$Zr(O_3POH)_{2/3}(O_3PCH_2CH=CH_2)_{4/3}.$$

25. An inorganic polymer as recited in claim 21 having the empirical formula:

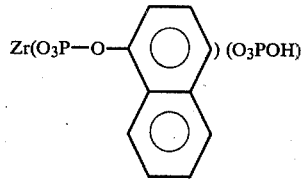

26. An inorganic polymer as recited in claim 22 having the empirical formula:

$$Zr(O_3POH)_{2/3}(O_3P(CH_2)_{10}PO_3)_{1/3}.$$

27. An inorganic polymer as recited in claim 21 having the empirical formula:

$$Zr(O_3PH)_{4/3}(O_3POCH_2CH_2CN)_{2/3}.$$

28. An inorganic polymer as recited in claim 21 having the empirical formula:

$$Zr(O_3PCH_3)_{4/3}(O_3PCH_2CH_2P\theta_2)_{2/3}.$$

29. An inorganic polymer as recited in claim 21 having the empirical formula:

$$Zr(O_3PCH_3)_{1.6}(O_3PCH_2CH_2CH_2P\theta_2)_{0.4}.$$

30. An inorganic polymer as recited in claim 21 having the empirical formula:

$$Zr(O_3POH)_{2/3}(O_3PCH_2Cl)_{4/3}.$$

31. An inorganic polymer as recited in claim 21 having the empirical formula:

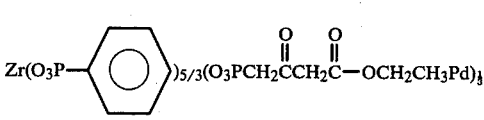

32. An inorganic polymer as recited in claim 21 having the empirical formula:

$$Zr(O_3P\theta)_{8/5}(O_3PCH_2CH_2CO_2H)_{2/5}.$$

33. An inorganic polymer as recited in claim 21 or 23 wherein the tetravalent metal is selected from the group consisting of zirconium, cerium, thorium, uranium, lead, hafnium and titanium.

* * * * *

UNITED STATES PATENT AND TRADEMARK OFFICE
CERTIFICATE OF CORRECTION

PATENT NO. : 4,429,111

DATED : January 31, 1984

INVENTOR(S) : Martin B. Dines, et al.

It is certified that error appears in the above-identified patent and that said Letters Patent is hereby corrected as shown below:

Column 1, line 17, change "43,910" to -- 43,810 --.

Column 3, line 37, change "11" to -- $\underline{11}$ --.

Column 3, line 42, change "23" to -- $\underline{23}$ --.

Column 3, line 43, change "20" to -- $\underline{20}$ --.

Column 3, line 48, change "15" to -- $\underline{15}$ --.

Column 3, line 60, change "40" to -- $\underline{40}$ --.

Column 3, line 68, change "15" to -- $\underline{15}$ --.

Column 4, line 32, change "meal" to -- metal --.

Column 5, line 49, change "M-tetravalent" to
-- M=tetravalent --.

UNITED STATES PATENT AND TRADEMARK OFFICE
CERTIFICATE OF CORRECTION

PATENT NO. : 4,429,111

DATED : January 31, 1984

INVENTOR(S) : Martin B. Dines, et al.

It is certified that error appears in the above-identified patent and that said Letters Patent is hereby corrected as shown below:

Column 6, line 22, change "compound"," to -- compound," --.

Column 6, line 29, change "phosphorous" to -- phosphorus --.

Column 9, line 13, change "phosphorous" to -- phosphorus --.

Column 9, line 25, change "phosphorous" to -- phosphorus --.

Column 10, lines 11-14, in Table II, under the title "Anchored Group" should be

--  $-O\sim CN$
  $\sim SH$
  $-O\sim CN$
  $-O\sim CN$  --.

Column 11, line 45, change "present" to -- product --.

Column 11, line 59, after "solution" and before the period add -- ) --.

Column 12, line 12, after THF and before the period add -- ) --.

Column 12, line 45, move "1.0" at the bottom of the bracket to the top of the bracket and before the formula to read -- $_{1.0}(O_3POH)_{1.0}$ --.

UNITED STATES PATENT AND TRADEMARK OFFICE
CERTIFICATE OF CORRECTION

PATENT NO. : 4,429,111

DATED : January 31, 1984

INVENTOR(S) : Martin B. Dines, et al.

It is certified that error appears in the above-identified patent and that said Letters Patent is hereby corrected as shown below:

Column 12, line 50, change "$._1H_2O$" to -- $·1H_2O$ --.

Column 13, line 15, move "1.0" at the bottom of the bracket to the top of the bracket and before the formula to read

-- $1.0^{(O_3POH)}1.0$ --.

Column 13, line 25, change "phosphorous" to -- phosphorus --.

Column 15, line 65, change "weight" to -- weighed --.

Column 16, line 33, delete "about" (second occurrence).

Column 16, line 49, change "phenol" to -- phenyl --.

Column 22, line 61, change "23" to -- 22 --.

Signed and Sealed this

Tenth Day of February, 1987

Attest:

DONALD J. QUIGG

Attesting Officer     Commissioner of Patents and Trademarks